(12) United States Patent
Drumm et al.

(10) Patent No.: US 10,894,222 B2
(45) Date of Patent: Jan. 19, 2021

(54) DISTRIBUTOR DEVICE, IN PARTICULAR FOR FALLING FILM EVAPORATORS, AND USE THEREOF

(71) Applicant: COVESTRO DEUTSCHLAND AG, Leverkusen (DE)

(72) Inventors: Christian Drumm, Frohnhofen (DE); Friedhelm Steffens, Leverkusen (DE); Dieter Hoffmann, Moers (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 16/485,492

(22) PCT Filed: Feb. 12, 2018

(86) PCT No.: PCT/EP2018/053397
§ 371 (c)(1),
(2) Date: Aug. 13, 2019

(87) PCT Pub. No.: WO2018/149776
PCT Pub. Date: Aug. 23, 2018

(65) Prior Publication Data
US 2020/0030712 A1 Jan. 30, 2020

(30) Foreign Application Priority Data
Feb. 14, 2017 (EP) .................... 17156032

(51) Int. Cl.
*B01D 1/06* (2006.01)
*B01D 1/00* (2006.01)
(Continued)

(52) U.S. Cl.
CPC ........... *B01D 1/007* (2013.01); *B01D 1/0094* (2013.01); *B01D 1/065* (2013.01); *B01D 1/30* (2013.01); *C07C 263/20* (2013.01)

(58) Field of Classification Search
CPC ...... B01D 1/007; B01D 1/0094; B01D 1/065; B01D 1/12; B01D 1/30; C07C 263/20
(Continued)

(56) References Cited

U.S. PATENT DOCUMENTS

| 1,916,314 A | * | 7/1933 | Hilger | .................. C07C 265/12 534/735 |
| 3,016,067 A | * | 1/1962 | Edmonds | .................. F28D 3/04 138/38 |
| 3,132,064 A | | 5/1964 | Hendrikus et al. | |

(Continued)

FOREIGN PATENT DOCUMENTS

| CN | 203342399 U | 12/2013 |
| CN | 203425542 U | 2/2014 |

(Continued)

OTHER PUBLICATIONS

International Search Report, PCT/EP2018/053397, dated Apr. 17, 2018, Authorized officer: Valerie Thibault.

*Primary Examiner* — Charles S Bushey
(74) *Attorney, Agent, or Firm* — Donald R. Palladino (57) ABSTRACT

The present invention relates to a distributor device (10000) for the even distribution of a fluid (10) into 2 or more fluid streams each containing gas (11) and liquid (12), with a falling film evaporator (100000), in which the distributor device according to the invention serves to distribute the 2 or more fluid streams onto the heating pipes of the evaporator, and to the use of the distributor device (10000) according to the invention and in particular the falling film evaporator (100000) according to the invention in the production and/or preparation of chemical products. The distributor device according to the invention is characterized, in particular, by a swirl breaker (600) for the gas phase (11) which arises from separating the fluid (10) into a gas phase (11) and a liquid phase (12) within the distributor device.

17 Claims, 8 Drawing Sheets

(51) Int. Cl.
 *C07C 263/20* (2006.01)
 *B01D 1/30* (2006.01)
(58) Field of Classification Search
 USPC .............................................. 261/110, 112.1
 See application file for complete search history.

(56) References Cited

U.S. PATENT DOCUMENTS

| | | | |
|---|---|---|---|
| 3,849,232 A | | 11/1974 | Kessler et al. |
| 3,880,961 A | * | 4/1975 | Alcock ................ B01J 8/0492 |
| | | | 261/16 |
| 4,094,734 A | | 6/1978 | Henderson |
| 4,134,939 A | * | 1/1979 | Zardi ..................... B01D 1/065 |
| | | | 261/112.1 |
| 4,154,642 A | * | 5/1979 | Mattern ................... C02F 1/08 |
| | | | 159/13.2 |
| 4,199,537 A | | 4/1980 | Lagana et al. |
| 4,932,468 A | * | 6/1990 | Ayub ....................... F28D 3/02 |
| | | | 159/13.2 |
| 5,004,043 A | * | 4/1991 | Mucic .................... B01D 1/065 |
| | | | 159/13.2 |
| 6,066,232 A | | 5/2000 | Mohr et al. |

FOREIGN PATENT DOCUMENTS

| | | |
|---|---|---|
| CN | 103980159 A | 8/2014 |
| CN | 204159052 | 2/2015 |
| DE | 1992031 U | 8/1968 |
| DE | 2103889 A | 9/1972 |
| DE | 279613 A | 6/1990 |
| DE | 29520263 U | 2/1996 |
| GB | 893633 A | 4/1962 |
| GB | 1209119 A | 10/1970 |

* cited by examiner

DISTRIBUTOR DEVICE, IN PARTICULAR FOR FALLING FILM EVAPORATORS, AND USE THEREOF

CROSS-REFERENCE TO RELATED APPLICATIONS

This application is a national stage application under 35 U.S.C. § 371 of PCT/EP2018/053397, filed Feb. 12, 2018, which claims the benefit of European Application No. 17156032.9, filed on Feb. 14, 2017, both of which are incorporated by reference herein.

FIELD

The present invention is concerned with a distributor device (10 000) for uniform division of a fluid (10) into 2 or more fluid streams each containing gas (11) and liquid (12), with a falling film evaporator (100 000), in which the distributor device of the invention serves for distributing the 2 or more fluid streams over the heating tubes of the evaporator and with the use of the distributor device (10 000) of the invention and in particular the falling film evaporator (100 000) of the invention in the production and/or work-up of chemical products. The distributor device of the invention is characterized, in particular, by a swirl breaker (600) for the gas phase (11) which is formed by separation of the fluid (10) into a gas phase (11) and a liquid phase (12) within the distributor devices.

BACKGROUND

Distributor devices for fluids which contain liquid and gaseous, in particular vapor, fractions or in the case of which a gas or vapor phase is formed in the distributor device by spontaneous evaporation are known in principle in the prior art. An important field of application for such distributor devices is their use in falling film evaporators. Falling film evaporators are widely used in industry, especially in vapor-liquid separation processes such as distillation or concentration by evaporation, with the vapor phase required for the separation of materials being produced in the falling film evaporator. Apart from pure separation of materials, evaporators can also serve for carrying out reactions. Thus, for example, CN 103 980 159 A discloses the use of a thin film evaporator in the pyrolysis of aminoalkyl esters.

In falling film evaporators, a relatively volatile component is evaporated from a liquid film flowing downward on the heated evaporator tubes. Uniform distribution of the liquid over the tubes is essential for correct operation of falling film evaporators, in order to ensure complete and permanent wetting of the tube wall (see Scholl, Rinner, 2006, *Verdampfung and Kondensation in Fluidverfahrenstechnik*, Goedecke (Ed.), Wiley). Liquid distributors which are installed in the cap above the upper tube plates of falling film evaporators and are designed for the specific case ensure the uniform distribution. In the case of boiling or supercooled liquids, the distributor should largely calm the liquid up to entry into the tubes and distribute it uniformly between and over the evaporator tubes. In the case of a superheated liquid, flash evaporation additionally occurs in the upper cap over the tube plate, so that not only the liquid phase but also a vapor phase, which depending on the degree of superheating and the pressure in the evaporator has a high velocity, is present. In this case, the liquid distributor has to be configured so that the vapor phase does not impair the effectiveness of the liquid distribution. This can, for example, be achieved by vapor and liquid being separated on their way into the evaporator tubes.

Particularly in the case of small amounts of liquid per evaporator tube, the evaporator can be operated in a circulation mode in such a way that part of the residual liquid exiting from the evaporator at the bottom is recirculated to the top of the evaporator. However, in the case of heat-sensitive products or when reactions (e.g. polymerization reactions) in the liquid can lead to formation of deposits or when liquids which from the beginning contain particles are to be evaporated, a single pass without circulation is generally desirable in order to keep the residence time in the evaporator and thus the probability of formation of deposits in the evaporator tubes low, which in turn tends to result in relatively small amounts of liquid in the tubes. The higher the evaporation ratio in the case of a small amount of liquid, the more important it is to supply each tube with the same amount of liquid. When the tubes are not uniformly supplied with liquid, problems such as excessive concentration and dry running through to blockage of individual tubes occur in the tubes which receive only a small amount of liquid, while in those tubes which receive too much liquid the desired final concentration is not achieved. In addition, in the case of excessive calming of the liquid in the systems described, formation of deposits in the region of the liquid distributor and the tube plate sometimes occurs, which ultimately lead to the same problems.

Apart from ensuring a very uniform distribution, it is also necessary for the liquid to form a stable film on the interior wall immediately after entry into the tube. The liquid must not drop through the tube or run down the tube in streams, but instead a uniform film which wets the entire available heating surface should be formed from the beginning.

Various variants are used as liquid distributors in the case of boiling or supercooled liquids. The most common variants are perforated box or perforated tank distributors, in which the liquid is distributed on the tube plate over a plurality of distributor stages (e.g. from 1 to 3 perforated plates or tanks with overflow at a serrated weir) between the evaporator tubes (e.g. U.S. Pat. No. 6,066,232, DE 29520263 U). In a further variant, the liquid runs from a distributor via an overflow through tubes on the smooth tube plate between the evaporator tubes (see U.S. Pat. No. 3,849,232), as a result of which blockages of the holes and deposits on the tube plate can be avoided. However, when no liquid level on the tube plate is realized, good distribution over the tubes cannot be assumed. Further customary variants provide distribution by means of nozzles (see, for example, CN 204159052 U, CN 203342399 U), distribution from a central tube over further small tubes (U.S. Pat. No. 4,094,734) and distribution over covering metal plates (DE 1126358 B, CN 203425542 U). Uniform distribution is in these variants partly assisted by flow calming.

In the case of spontaneous evaporation of an inflowing superheated liquid or an inflowing gas (or vapor)/liquid mixture, flash chambers or vapor/liquid separators, which in the simplest case are configured as impingement plate and provide separation of the phases, before the liquid is distributed further via suitable distribution variants have been described, but all of these systems which tend to form deposits (known as fouling) are not optimal. DE 1126358 B describes two variants in which the vapor/liquid separation takes place in an upper impingement plate. The liquid runs over a covering plate into a tank distributor which distributes the liquid via dripping positions over the tube plate and produces a liquid level in the tank in order to calm the flow. The vapor is, at the tank distributor, either conveyed past on the outside and flows from the outside inward onto the tube plate and into the tubes or is conveyed through a central tube through the middle onto the tube plate.

In a further variant, the vapor flows from the flash chamber directly into tubes which protrude into the evaporator tubes. The liquid which is not entrained by the vapor collects on a perforated plate, whose drip positions are arranged between the evaporator tubes (CH 385169 A).

DE 2103889 A1 describes a solution in which flash evaporation takes place in a flash space (tanks with serrated weir). The vapor flows through a central tube from above into a vapor collection space and subsequently into tubes which protrude directly on the tube plate centrally into the evaporator tubes. The liquid flows over a serrated weir onto the lid of the vapor collection space and goes from outside onto the tube plate, but no liquid level on the tube plate is provided, so that good liquid distribution cannot be assumed.

DE 1992031 U describes a distributor system having a feed pot and two perforated tank distributors located underneath, with a high liquid level and flow calming being desired. If vapor is formed by spontaneous evaporation, this can escape upward in the feed pot and goes via an outer gap between the lower tank distributor and the cap wall onto the tube plate.

In DD 279613 A, a liquid-vapor mixture is conveyed into a separating tank in which the two phases can separate. In the separating tank there are overflow tubes for the liquid through which the liquid flows onto the tube plate, with the end of the tube being located just above the tube plate below the surface of the liquid. The vapor is again conveyed along the outside of the separating tank and flows inward to the tubes. In this variant, entrainment of droplets by the vapor phase flowing past is avoided by means of the immersion.

In DE 2604389 (also published as U.S. Pat. No. 4,154, 642), a tangential entry (3 in the drawings) in an outer annular gap (4) in which vapor and liquid can separate is provided. Vapor rises upward and then flows through an internal cylinder (6), which widens in a downward direction in a cone-like manner downward again and there directly into the heating tubes (2). The heating tubes (2) are surrounded by a cylinder (6b in the drawings of the US equivalent) which is connected to the cone-shaped transition piece. Neither the cylinder (6) nor the cone-shaped transition piece have internals of any type. The liquid flows downward in the outer annular gap (4) and through a gap (7) formed by the inside of the bounding wall of the apparatus and the cylinder (6b) onto the tube plate (11) where a high liquid level within the cylinder (6b) is realized by the heating tubes (2) protruding far beyond the tube plate (11) (readily visible in FIG. 1A of the US equivalent, "Lb"). The flow of the liquid into the heating tubes (2) then occurs just above the tube plate (11) through openings (8) in the tubes (2) in order to ensure uniform distribution of liquid. Although no problems are to be expected in respect of the liquid distribution in the distributor of DE 2604389, due to the high liquid level and the inflow below the liquid surface, the distributor is no longer suitable for systems which tend to form deposits because of the excessive calming. A swirl breaker for the vapor phase is not disclosed in the application.

U.S. Pat. No. 4,199,537 is concerned with the problem of ensuring uniform distribution of liquid on the insides of the tubes in shell-and-tube apparatuses (e.g. heat exchangers). For this purpose, a description is given of a liquid distributor in which the liquid to be distributed is introduced via an inlet port (7 or 7' in the drawings) through a ring having openings (6) into a gap between an inner bell-shaped cover (5) and the inside of the bounding wall (1) of the apparatus. From this gap, the liquid flows onto the tube plate (3) from where it runs through holes in feed or distributor shells (4) into the tubes (2). As a result of the inflow via the holes having preferred diameters of from 2 to 4 mm, a relatively high liquid level (27) is produced in this invention, too (see FIG. 4). Like the distributor described in DE 2604389, this distributor also tends to form deposits on the tube plate and suffer from blockage of the small holes in the case of systems which are susceptible to fouling. A swirl breaker for the vapor phase is not disclosed in this document either.

Neither in U.S. Pat. No. 4,199,537 nor in DE 2604389 described further above (also published as U.S. Pat. No. 4,154,642), can the heating tubes ("2" in both documents) or the distributor shells ("4" in U.S. Pat. No. 4,199,537) be considered to be swirl breakers for the gas phase. Turbulence, swirl or rotational velocities in the gas phase are reduced only after distribution of the liquid over the individual tubes (2).

The German first publication DE 1 769 607 (also published as GB 1 209 119) is concerned with a tube overflow which ensures uniform distribution of liquid over the tubes in an evaporator having a falling film. The overflow has a tubular extension which has one or more upward-extending slits (14) in the wall and inward-directed lobes (16), so that the liquid is on entry guided in a tangential direction onto the inside of the tube. The overflows described in DE 1 769 607 correspond to the "guide devices (800")" (e.g. tube spouts) described further below in the present invention. Height differences in the liquid level on the tube plate can be equalized by means of tube spouts having slits at the tube inlet without tremendous incorrect distribution over the tubes occurring. At the same time, wetting on the inside of the evaporator tubes is ensured.

In industrial practice, it has been found that the solutions described in the literature for uniform distribution of liquid have substantial disadvantages in systems which tend to form deposits. The formation of deposits (also referred to as fouling) can be attributable to a variety of causes, e.g. solid particles in the liquid to be vaporized, polymerization and cracking in the evaporator due to an excessively long residence time and crystallization (for example of dissolved salts) in the case of supersaturated liquids and sometimes also formation of algae ("biofouling"). At high liquid levels on the tube plate and in perforated tanks, tremendous deposits occur because of excessive flow calming. Holes in perforated plates for liquid distribution and holes on the tube inlet tend to become blocked. When, on occurrence of spontaneous evaporation due to depressurization, the vapor is conveyed past between the distributor and the inner cap wall and flows inward to the tubes, entrainment of the liquid dripping downward generally occurs. When the liquid is conveyed through tubes (known as "down comers") from the main distributor directly below the liquid surface onto the tube plates in order to avoid this entrainment of droplets by the vapor flowing past, these tubes also tend to become blocked at the tube outlet just above the tube plate (see DD 279613 A above). Wetting can likewise not be considered to be optimal in the case of direct inflow centrally into the tubes or a smooth tube plate. When no liquid level is realized on the tube plate in order to avoid deposits, good liquid distribution can likewise not be assumed.

There is therefore a need for further improvements in the design of distributor devices for fluids which contain liquid and gaseous (in particular vapor) fractions or in the case of which a vapor phase is formed in the distributor device by flash evaporation. In particular, it would be desirable to avoid both the formation of deposits due to excessive liquid levels and flow calming and also incorrect distribution due to excessively high velocities in the vapor and liquid phases and/or due to lack of a liquid level. Furthermore, it would be desirable to separate vapor and liquid in such a way that entrainment of droplets does not occur and the inflow of liquid is not impaired.

SUMMARY

Taking into account this need, the present invention provides a distributor device (10 000) suitable for uniform division of a fluid (10) into n fluid streams each containing gas (11) and liquid (12), where n is a natural number greater than or equal to 2, preferably from 2 to 1000, particularly preferably from 2 to 200, very particularly preferably from 4 to 100, where the device (10 000) comprises the following:
- an upright cap (100), preferably having a rotationally symmetric, particularly preferably round, in particular circular cross-sectional area which is bounded at the bottom by a plate (900);
- an entry port (200) for a fluid (10) arranged in a lateral delimiting wall of the cap (100), which entry port (200) is configured so that tangential inflow of the fluid (10) is brought about;
- an internal (300) arranged upright in the interior of the cap, preferably having a rotationally symmetric, particularly preferably round, in particular circular cross-sectional area,
  - which together with the interior wall of the cap (100) forms an annular gap (400) for downflowing liquid (12),
  - whose upper edge ends above the entry port (200) and below the upper delimitation of the cap (100) so that the upper edge of the internal (300) and the upper delimitation of the cap (100) form a passage (510) for gas (11),
  - which at the top has at least one opening (310) for inflowing gas (11),
  - whose lower edge ends above the plate (900) so that the lower edge of the internal (300) and the plate (900) form a passage (520) for liquid (12) and
  - which at the bottom has at least one opening (320) which is hydrodynamically connected to the at least one upper opening (310);
- n guide devices (800) for n fluid streams composed of liquid (12) and gas (11), which guide devices (800) protrude through the opening (320) into the internal (300) and have entry openings (810) for liquid (12) (preferably in each case from 2 to 10, particularly preferably from 4 to 8, entry openings (810)) and entry openings (820) for gas (11);
where a swirl breaker (600) for downward-flowing gas (11) is arranged in the interior of the internal (300).

The present invention further provides a falling film evaporator (100 000) in which the distributor device (10000) of the invention is used for uniformly dividing a fluid (10) to be evaporated into n fluid streams each containing gas (11) and liquid (12).

The present invention further provides for the use of the falling film evaporator (100 000) of the invention in the production or work-up of a chemical product selected from the group consisting of organic nitro compounds, primary organic amines, isocyanates, polyether polyols and polycarbonates.

BRIEF DESCRIPTION OF THE DRAWINGS

Various features and characteristics of the inventions described in this specification may be better understood by reference to the accompanying figures, in which.

DETAILED DESCRIPTION

For the purposes of the present invention, "(arranged) upright" means that the corresponding apparatus or the corresponding apparatus part is oriented substantially vertically. Of course, a completely vertical orientation is preferred. However, due to manufacturing tolerances, deviations from a completely vertical orientation, in particular in the range up to ±3.0°, preferably up to ±2.0°, particularly preferably up to ±1.0°, can occur in practice. Such slight deviations of course do not go outside the scope of the present invention.

A cross-sectional area is, for the purposes of the invention, "rotationally symmetric" when the cross-sectional area can be brought to coincide with itself on rotation by an angle $\alpha$ around an axis oriented perpendicular to the area and running through the center of gravity of the area, where a is one or more angle(s) different from 360° (cross-sectional areas which can be brought to coincide with themselves solely on rotation by 360° are therefore not rotationally symmetric). It goes without saying that this applies to any cross-sectional area of the apparatus or apparatus part in question. The simplest (and in all embodiments of the invention most preferred) way of configuring the distributor device (10 000) of the invention, the internal (300) and naturally also the falling film evaporator (100000) of the invention in rotationally symmetric form in this sense is construction of all these apparatuses or apparatus parts as hollow cylinders. Of course, slight manufacturing-related deviations from the ideal cylinder geometry do not go outside the scope of the invention. For the purposes of the present invention, devices (e.g. the entry ports (200) on the cap (100)) installed on the respective apparatus or apparatus part of course do not count as deviation from a rotationally symmetric configuration since the interior of the respective apparatus or apparatus part is decisive (i.e. it is the internal cross section of the respective hollow body which is taken into account).

In the distributor device (10 000) of the invention, a division of a "fluid (10)" in "n fluid streams each containing gas (11) and liquid (12)" takes place. Here, the fluid (10) can be a liquid (e.g. a liquid which has been superheated in respect of at least one of its constituents) which on entry into the distributor device (10000) of the invention partially vaporizes as a result of a pressure reduction (depressurization) (flash evaporation; also referred to as spontaneous evaporation). In this case, the "gas (11)" is the vapor formed on partial vaporization of the fluid (10) and the liquid (12) is the remaining ("residual") liquid which has not been vaporized in the distributor device (10 000). (For the purposes of the present invention, the term "vapor" is the gaseous phase formed on vaporization of a liquid, while the term "gas" can encompass not only the "vapor" formed from the liquid but also further gaseous constituents.) The fluid (10) can, however, be present from the beginning as a gas/liquid mixture (either because part of the liquid is present as vapor even before entry into the distributor device (10 000) or because a foreign gas such as an inert gas such as nitrogen added to effect dilution or a gaseous by-product or coproduct dissolved in a product mixture is present) whose gas components are separated from the liquid components in the distributor apparatus (10 000). Of course, spontaneous evaporation can additionally occur in this case, as a result of which vapor is formed by partial vaporization in the distributor device (10 000) in addition to the vapor or foreign gas which is present from the beginning. It is likewise possible to feed in a further fluid stream (e.g. a further gas stream) separately via a further entry port. In this case, separation into a gas phase (11) and a liquid phase (12) takes place in the distributor device (10 000). Gas (11) and liquid (12) pass through the distributor device (10 000) separately from one another (namely in the interior of the internal (300) or in the annular gap (400)) and thus form the "n fluid streams containing gas (11) and liquid (12)" on entry into the n guide devices (800). The "n guide devices (800)" serve, in the context of the invention, to divide the fluid into n fluid streams and when the distributor device of the invention is used in a falling film evaporator connected to the tubes of the falling film evaporator (or are the upper ends of the tubes). The n guide devices (800) are in particular fastened in the plate (900) (preferably welded).

Figure 2A:
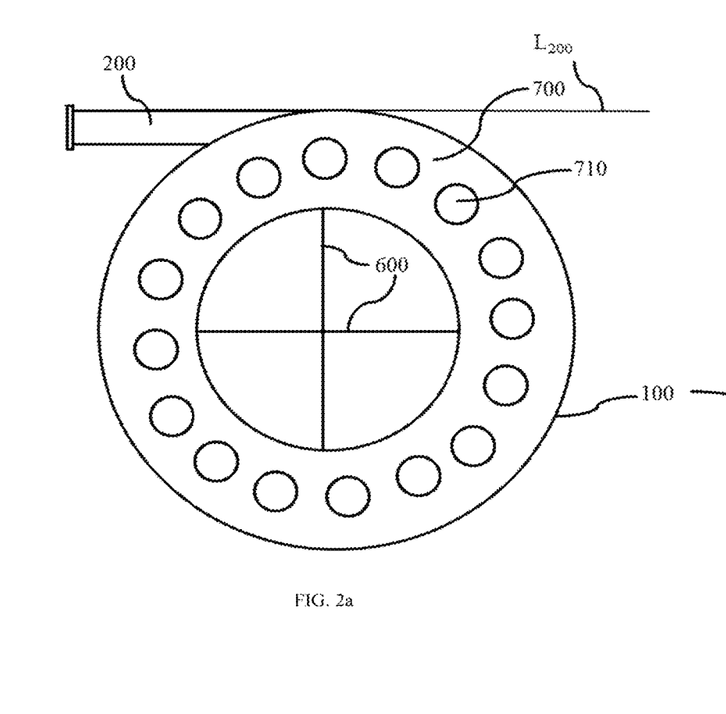
FIGS. 2a and 2b illustrate embodiments of a swirl breaker suitable for use in the distributor device of the invention.
Figure 2B:
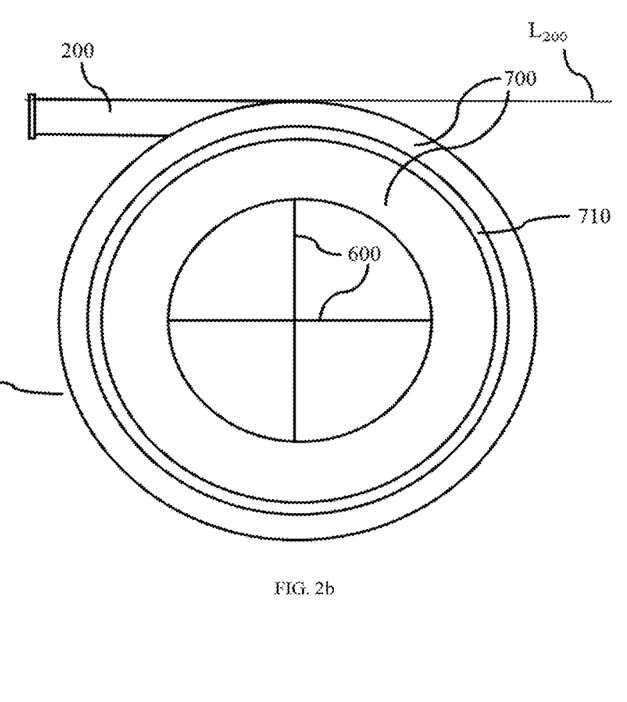
Figure 3:
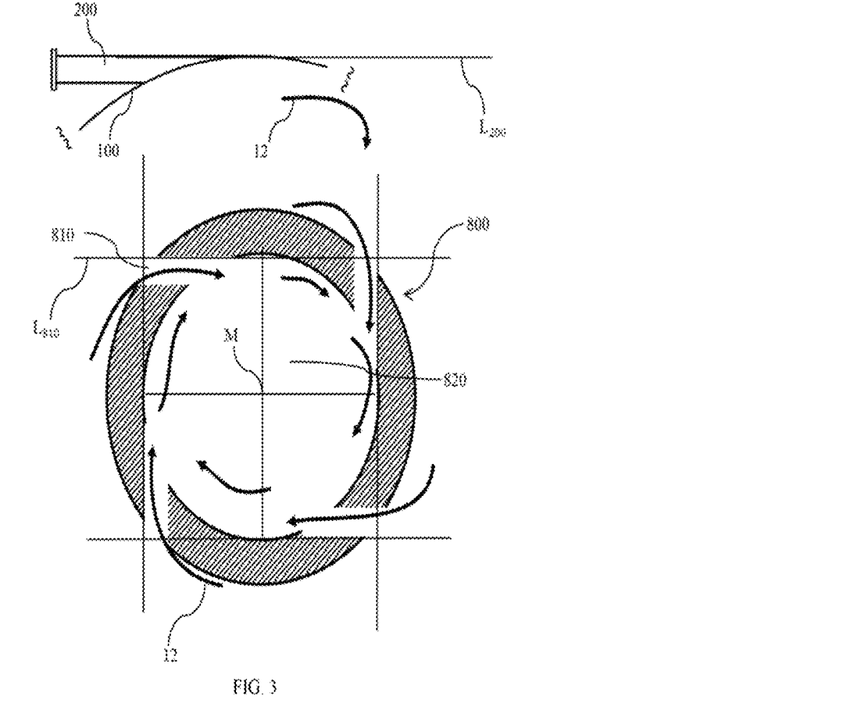
FIG. 3. illustrates a plan view of an embodiment of a guide device suitable for use in the distributor device of the invention.

The entry port (200) (essentially a hollow cylinder) is configured so that "tangential inflow of the fluid (10) is brought about", which is in particular the case when, viewed in plan view, a straight line drawn along the longitudinal axis of the entry port (200) on its interior delimiting wall forms a tangent to the interior surface of the cap (100), as shown in FIG. 2a, b and in the upper part of FIG. 3 (cf. the straight lines $L_{200}$; the drawings are not true to scale).

It has, completely surprisingly, been found that, for example, the distributor described in DE 2604389 (also published as U.S. Pat. No. 4,154,642) cannot be made suitable for systems which tend to form deposits simply by not making the tubes protrude so far beyond the tube plates and instead of an inflow through holes realizing an overflow as in DE 1 769 607 in order to reduce the liquid level on the tube plate and thus avoid excessive calming of the liquid. This is because high velocities and high turbulence in the vapor phase and liquid phase arise in the distributor described because of the tangential entry and the spontaneous evaporation. The vapor phase does not move only downward toward the tubes in the inner cylinder but is at the same time subject to strong rotational motion. At the same time, the liquid also undergoes rotational motion in the outer gap because of the tangential entry. The turbulence in the vapor phase leads to high flows at the tube entrance and breaking up of the liquid surface around the heating tubes. The high velocities and turbulence in vapor and liquid surprisingly result in tremendous incorrect distribution of the liquid over the evaporator tubes, which becomes greater with increasing proportion of vapor since the turbulence in the vapor phase disrupt the liquid inflow. These problems are reduced or even eliminated by the use according to the invention of the swirl breaker (600). For the purposes of the invention, a "swirl breaker" is an apparatus which is able to reduce or eliminate turbulence in a stream, to reduce the rotational energy of a flow and to make the flow uniform. In the simplest case, this can be two or more metal plates which are welded onto a swirl cross and thus prevent rotational motion of the fluid (see FIG. 4.7 Vortex breakers prior to installing in Plant Design and Operations, Chapter 4, Piping, page 162, I. Sutton (Author), 2017, Elsevier). Many further variants such as perforated plates and deflection plates, (structured) packings and knitted meshes, which depending on arrangement can eliminate turbulence or rotational motion in the fluid, are conceivable. The swirl breaker (600) according to the invention for downflowing gas is arranged in the interior of the internal (300), namely, as can readily be seen in the drawings (see FIG. 1 and FIG. 5), in a region of this in which the downward-flowing liquid (12) is separated from the downward-flowing gas (11), i.e. (significantly) above the passage (520) for liquid (12).

A summary of various possible embodiments of the invention firstly follows:

In a first embodiment of the invention, which can be combined with all other embodiments, the cross section of the internal (300) widens in a downward direction, which, in the particularly preferred embodiment of the internal (300) as body having a circular cross-sectional area, means that the internal (300) has a conical-cylindrical shape, which will be explained in more detail further below.

In a second embodiment of the invention, which can likewise be combined with all other embodiments of the invention, a swirl breaker (700) for liquid (12) having through-openings (710) for the liquid (12) is arranged in the annular gap (400) below the entry port (200).

In a third embodiment of the invention, which is a particular variant of the second embodiment, the swirl breaker (700) for liquid (12) is a metal plate in which the through-openings (710) for liquid (12) are formed by at least two holes which are in particular distributed uniformly over the entire area of the plate and/or by at least one slit which, in particular, runs through the entire area of the plate.

In a fourth embodiment of the invention, which can be combined with all other embodiments of the invention, the opening (310) for inflowing gas (11) extends over the entire internal cross section of the internal (300).

In a fifth embodiment of the invention, which can likewise be combined with all other embodiments of the invention, the opening (320) through which the n guide devices (800) extend into the internal (300) extends over the entire internal cross section of the internal (300). The fourth and fifth embodiments can be realized most advantageously by the internal (300) being configured as hollow cylinder.

In a sixth embodiment of the invention, which can be combined with all other embodiments of the invention, the n guide devices (800) are tube spouts or constituents of tubes (1000).

In a seventh embodiment of the invention, which is a particular variant of the sixth embodiment, the entry openings (810) for liquid (12) are tangential slits which are, in particular, arranged so that the flow of the liquid (12) produced on the inside of the guide devices (800) has the same direction as the flow of the liquid (12) produced in the annular gap (400) by the arrangement of the entry port (200) or axial slits.

In an eighth embodiment of the invention, which can be combined with all other embodiments of the invention, the swirl breaker (600) for downward-flowing gas (11) is selected from the group consisting of swirl crosses, packings, knitted wire meshes, perforated plates and deflection plates.

In a ninth embodiment of the invention, which can be combined with all other embodiments of the invention, the n guide devices (800) protrude to a height H in the range from 10 mm to 100 mm, preferably in the range from 20 mm to 50 mm, into the internal (300).

In a tenth embodiment of the invention, which can be combined with all other embodiments of the invention, the distributor device (10000) of the invention is the distributor device at the top of a falling film evaporator (100 000). The falling film evaporator (100000) of the invention comprises the following:

an outer, enclosing shell (2000),
n tubes (1000) which are fastened in an upper tube plate and a lower tube plate, where n is a natural number greater than or equal to 2, preferably from 2 to 1000, particularly preferably from 2 to 200, very particularly preferably from 4 to 100, on the inside of which a liquid film can flow down,
the device (10 000) of the invention as upper distributor device for distributing liquid (12) and gas (11) into the individual tubes (1000), where the bottom (900) of the device (10 000) forms the upper tube plate of the falling film evaporator (100 000) and the n guide devices (800) of the device (10000) are connected to the n tubes (1000) at their upper end or are constituents of the n tubes (1000),
a feed device (3100) for feeding a heating medium (20), preferably steam, pressurized water, oil or a salt melt, in particular steam, into the tube exterior space formed by the outside of the tubes (1000) and the shell (2000),
a discharge device (3200) for discharging cooled heating medium (21), in particular condensed water, from the tube exterior space,
a vapor offtake device (4100) for vapor (13),
a liquid offtake device (4200) for residual liquid (14) which has not been vaporized inside the tubes,
a device (5000) for separating and collecting residual liquid (14) and vapor (13).

In an eleventh embodiment of the invention, which is a particular variant of the tenth embodiment, the falling film evaporator (100 000) has a return device (6000) for recirculating part of the residual liquid (14) into the distributor device (10 000), where this return device (6000)

comprises a mixing device (6100) for mixing the recirculated part of the residual liquid (14) with the fluid (10) before entry into the distributor device (10 000), or
opens into an entry port (210) which is different from the entry port (200) and is arranged in a lateral delimiting wall of the cap (100).

In a twelfth embodiment of the invention, which can be combined with all other embodiments of the invention, the use of the distributor device (10 000) of the invention or of the falling film evaporator (100 000) of the invention concerns the production and/or work-up of a chemical product selected from the group consisting of organic nitro compounds, organic primary amines, isocyanates, polyether polyols and polycarbonates.

In a thirteenth embodiment of the invention, which is a particular variant of the twelfth embodiment, the falling film evaporator (100000) is used in the work-up of an isocyanate for vaporization of the latter.

In a fourteenth embodiment of the invention, which is a particular variant of the thirteenth embodiment, the vaporization of the isocyanate is used for at least partially removing the isocyanate from a residue-containing distillation bottom stream from isocyanate production and/or for separating a monomeric isocyanate fraction, which is vaporized, from a polymeric isocyanate fraction.

In a fifteenth embodiment of the invention, which is a particular variant of the thirteenth and fourteenth embodiments, the isocyanate is selected from the group consisting of tolylene diisocyanate, the diisocyanates and polyisocyanates of the diphenylmethane series, hexamethylene diisocyanate, pentamethylene diisocyanate, isophorone diisocyanate, xylylene diisocyanate, naphthalene diisocyanate and dicyclohexylmethane diisocyanate.

The embodiments briefly indicated above and further possible variants of the invention are explained in more detail below, in particular with the aid of the accompanying drawings. In the drawings, the invention is explained for the example of a liquid fluid (10) which on entry into the distributor device (10 000) partially vaporizes, forming vapor and leaving unvaporized liquid; the reference numeral 11 will for this reason be used in the following description for vapor and the reference numeral 12 will be used for unvaporized ("residual") liquid. However, the invention is not restricted thereto, but also encompasses, for example, the case where the fluid (12) is from the beginning present as gas/liquid mixture (11, 12) or a gas phase (11) is fed in separately, as has been explained above. Thus, when the expression vapor (11) (formed by partial vaporization of the fluid (12)) is used in the following, the same always applies, unless indicated otherwise, to any gas (11) (e.g. a foreign gas added, for instance an inert gas such as nitrogen added to effect dilution or a gaseous by-product or coproduct dissolved in a product mixture).

Various embodiments can, unless the contrary is not obvious to a person skilled in the art from the context, be combined with one another in any way. The accompanying figures serve to illustrate the invention; they do not claim to be true to scale.

Figure 1:
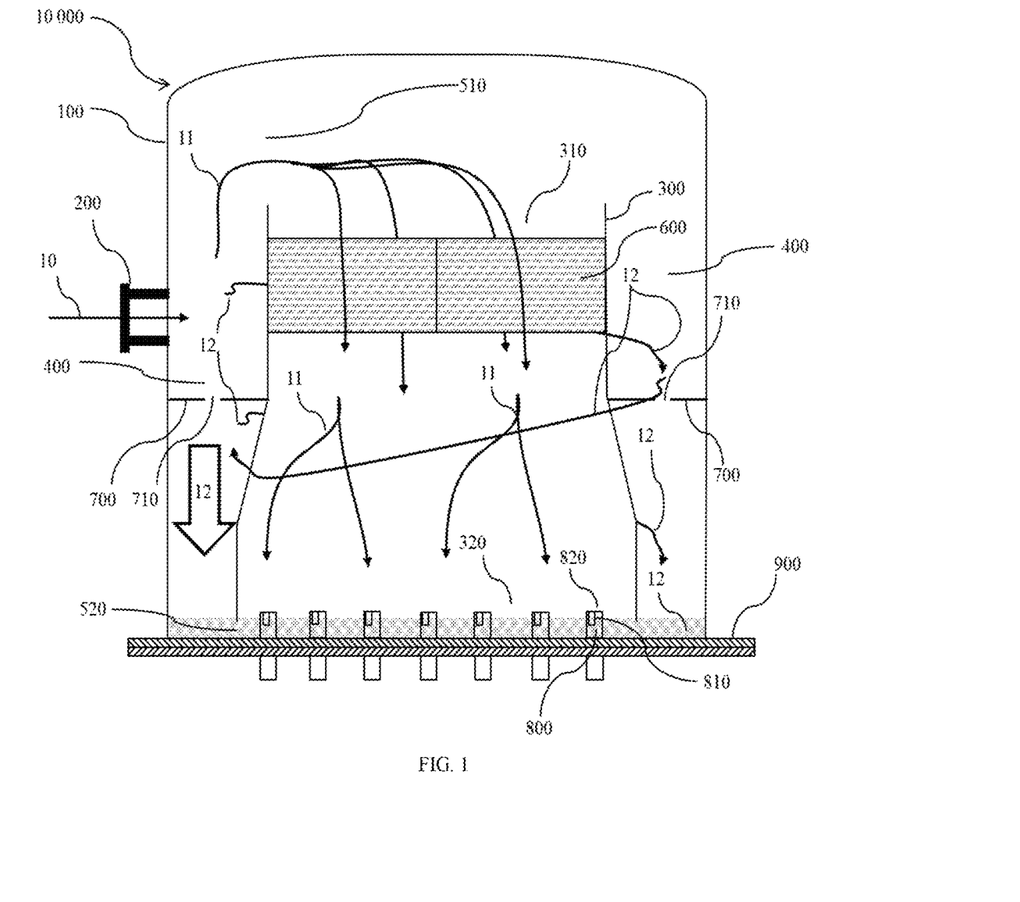
FIG. 1 illustrates an embodiment of the distributor device of the invention.

FIG. 1 shows a preferred embodiment of the distributor device (10 000) of the invention. The distributor device has at least one inlet (200) which allows tangential inflow of the fluid (10) (known as "tangential port"). The tangential entry occurs into an annular gap (400) which is formed by the interior wall of the cap (100) and the outer wall of the internal (300). In the embodiment shown in FIG. 1, the internal (300) consists of an upper hollow cylinder and a lower hollow cylinder having a greater cross-sectional area, which are joined to one another by means of a conical transition piece ("conical-cylindrical shape"). This embodiment having a widening cross section of the internal (300) is preferred. In this embodiment, the swirl breaker (600) for downward-flowing gas is arranged in the upper cylindrical part (in the upper hollow cylinder) of the internal (300), as can readily be seen in FIG. 1 and FIG. 5. The at least one upper opening (310) and the at least one lower opening (320) then in each case correspond to the entire internal cross section of the upper or lower cylinder, respectively. This is the preferred configuration of these openings. However, it is also conceivable to use a simple hollow cylinder having a constant cross section as internal (300).

This internal (300) protrudes to beyond the entry port (200) in order to avoid entrainment of droplets. Spontaneous evaporation occurs in the region of the entry port (200) since the inflowing fluid is depressurized to the pressure in the distributor device (10 000), which is lower than the pressure under which the fluid (10) is before entry into the distributor device (10 000). (If the fluid (10) is present from the beginning as gas/liquid mixture, separation of gas and liquid as described below simply occurs.) Since the liquid is pushed against the outer wall (the interior wall of the cap (100)) (tangential inflow), the desired separation of vapor (11) and liquid (12) occurs in the annular gap (400) because of the density differences. The vapor (11) can flow unhindered upward and travels through the passage (510) in the internal (300) and through this to the bottom (900) where it enters the n guide devices (800) through the opening (820). These guide devices (800) can, for example, be tube spouts or else (fixed) constituents of tubes (i.e. the upper ends of tubes). Tube spouts can also be referred to as spouts, distributor sheaths or feed sheaths.

The preferred configuration of the internal (300) with a conical-cylindrical shape with a cross section which widens in the downward direction ensures that the annular gap (400) is wider (i.e. a greater cross-sectional area is available) in the region of spontaneous evaporation than in the lower region of the distributor device where the liquid (12) passes through the passage (the gap) 520 and the internal (300) encloses the n guide devices (800). In this way, the vapor (11) can distribute itself over the n guide devices (800).

The internal (300) ends at a small distance above the bottom (900) and forms a passage (a gap) (520). The liquid (12) flows downward in the outer annular gap (400) (symbolized by the block arrow in FIG. 1) and through the gap (520) between bottom (900) and the lower edge of the internal (300) in an inward direction on the bottom (900) and runs through the openings (810) into the n guide devices (800). The liquid (12) is sent into rotation by the tangential port (200) and by the spontaneous evaporation with high vapor velocities and follows a circular path in the annular gap (400) (indicated by continuous thin arrows in FIG. 1) which goes down to the bottom (900).

Our own experimental studies on distributor devices of the prior art (without the swirl breaker (600)) have shown that the velocity and turbulence in the liquid (12) which flows with circular motion in the annular gap (400) onto the bottom (900) become ever stronger with increasing vaporization of the fluid (10) (depending on the degree of superheating). This circular flow continues down to the bottom (900). The strong flow prevents the formation of deposits on the bottom (900). Furthermore, our own experiments showed strong turbulence in the downward-flowing vapor phase (11) in the inner internal (300). This turbulence again disturbs uniform distribution of the liquid (12) over the n guide devices (800). Owing to the strong flow, the uniform inflow of the liquid into the guide devices (800) is disrupted, so that the amount of liquid per guide device (800) can fluctuate greatly. It has been found here that, in particular, the outer guide devices (800) in the region having the greatest turbulence receive the smallest amount of liquid, while the inner guide devices (800), where flow calming has occurred, receive the greatest amounts of liquid (see examples).

According to the invention, a suitable swirl breaker (600) for the vapor phase (11) is installed in the inner internal (300) in order to solve this problem. A swirl cross can here serve as swirl breaker (600), as shown in FIG. 1. This preferably has at least three blades (e.g. precisely 3 blades), particularly preferably at least four blades (e.g. precisely 4 blades, as shown in FIG. 2a, b in which the swirl cross can be seen in plan view), extraordinarily very particularly preferably at least 8 blades (e.g. precisely 8 blades). The upper limit to the number of blades is in principle limited only by the fact that sufficient flow of the vapor (11) still has to be ensured and can easily be determined by a person skilled in the art for a given case. Such a swirl cross eliminates the circular flow and turbulence in the vapor phase. In addition, metal packings, knitted wire meshes, perforated plates or, in particular offset, deflection plates are also possible as swirl breakers (600). In our own experiment, the turbulence in the vapor phase (11) could be eliminated in this way and the liquid distribution was significantly improved (see examples).

To prevent the liquid coming from the entry port from impinging on the surface of the liquid at only one place in the lower annular gap (400), which could in turn lead to turbulence, entrainment of gas and ultimately incorrect distribution in the region of the lower gap (520) and the openings (820) for inflow of liquid, preference is given to ensuring predistribution and precalming of the liquid in the annular gap (400). The annular gap (400) is for this reason preferably to be provided with a swirl breaker (700) for liquid (12) below the entry port (200). This swirl breaker (700) for liquid is in the simplest case a continuous metal sheet having openings (710) through which the liquid (12) can flow out. Depending on the fouling tendency of the system, these openings can be realized by a number of holes (FIG. 2a) or by a (preferably continuous) narrow slit (FIG. 2b). Depending on the diameter and number of the holes or the width of the slit, a (small) liquid level can additionally be produced on the swirl breaker (700), which likewise contributes to calming the flow somewhat and distributing it over the entire circumference without completely eliminating the momentum. In the case of a strong fouling tendency, the variant having a narrow slit (FIG. 2b), which barely calms the flow, so that deposits on the tube plate are avoided, but the liquid (12) can distribute itself over virtually the entire circumference by flowing through the slit, is preferably used. In the case of a lower fouling tendency, the variant having a plurality of holes (FIG. 2a) can be selected, with the number and diameter of the holes being able to be calculated easily by a person skilled in the art so that a liquid level is established on the swirl breaker (700). In this variant, the flow is, depending on the liquid level, calmed more strongly and the swirl or circular flow is virtually completely broken.

The liquid level on the bottom (900) is preferably kept small in order to avoid deposits due to excessively low velocities of the liquid (12). This is achieved by configuring the device (10 000) in such a way that the n guide devices (800) extend to a height H (cf. FIG. 4) in the range from 10 mm to 100 mm, preferably in the range from 20 mm to 50 mm, into the internal (300).

FIG. 3 shows a plan view of a guide device (800) in a preferred embodiment. The guide device (800) here corresponds to an upright hollow cylinder (tube spout or (fixed) constituent of a tube) whose upper (open) side forms the entry opening (820) for vapor (11). In principle, the liquid (12) can simply be allowed to overflow over the upper edge of the hollow cylinder (the entry opening 820 is then identical to the entry opening 810); however, preference is given, as shown in FIG. 3, to providing dedicated entry openings (810) which are arranged at the end of the n guide devices (800) protruding into the internal (300) for entry of the liquid (12). The guide devices (800) preferably each have from 2 to 10, particularly preferably from 4 to 8, (dedicated) entry openings (810). In the embodiment shown in FIG. 3, the entry openings (810) are configured as tangential slits. Here, tangential slits are slits which allow tangential inflow of the liquid (12). This is the case particularly when a straight line drawn along the longitudinal axis of the slit at its inner delimiting wall forms a tangent to the internal surface of the guide device (800) (the hollow cylinder), as shown in FIG. 3 (cf. the straight line $L_{810}$). However, the use of axial slits in the case of which a straight line drawn centrally through the slit along the longitudinal axis of the slits goes through the midpoint M of the hollow cylinder is likewise possible.

Tangential slits are preferred. Here, particular preference is given to the flow produced by the tangential slits on the inside of the guide devices (800) (in particular circular flow) of the liquid (12) being oriented the same way (has the same direction) as the flow (in particular cross-flow) of the liquid (12) which is produced by the tangential arrangement of the entry port (200) in the annular gap (400). Both flows thus run, viewed from above, as in FIG. 3, either clockwise or counterclockwise. In FIG. 3, the tangential port produces a clockwise flow which is also propagated into the guide devices (800) by correct installation of the tangential slits in the hollow cylinder (800). This arrangement of the tangential slits promotes unhindered inflow of the liquid (12) into the entry openings (810) and from there into the hollow cylinder (800) where the liquid (12) is, as desired, directed onto the interior wall of the hollow cylinder (800) and there forms a stable liquid film. In the case of the opposite orientation of the slits, disruption of the flow at the entry into the hollow cylinder, which would hinder formation of a stable liquid film, cannot be ruled out.

Figure 4:
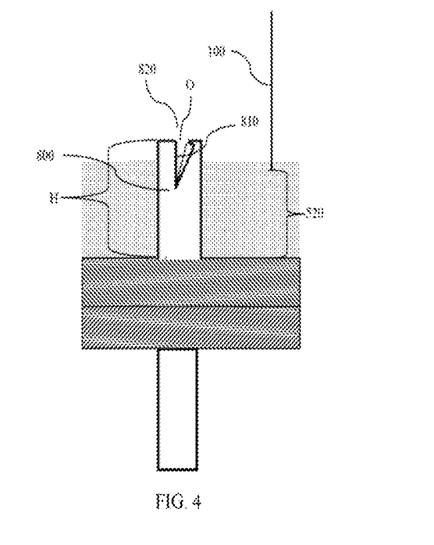
FIG. 4 illustrates a triangular shaped liquid entry opening according to an embodiment of a guide device suitable for use in the distributor device of the invention.

The lateral shape of the entry openings (810) is in principle not restricted. Apart from a rectangular shape, a triangular shape as depicted in FIG. 4 is also conceivable. For this purpose, the hollow cylinder (800) can, for example, simply be cut into at its upper end and an entry opening (810) having a triangular lateral area can be formed by folding over (known as folded-open slit).

Regardless of the lateral shape of the entry openings (810), it is in every case preferred that they are open at the top as shown by way of example in FIG. 4 for a folded-open slit having a triangular lateral area (see "O" in FIG. 4).

As mentioned at the outset, the distributor device (10 000) of the invention is particularly suitable for use in a falling film evaporator. The invention therefore further provides a falling film evaporator (100 000) (cf. FIG. 5) comprising
an outer, enclosing shell (2000),
n tubes (1000) which are fastened in an upper tube plate and a lower tube plate, where n is a natural number greater than or equal to 2, preferably from 2 to 1000, particularly preferably from 2 to 200, very particularly preferably from 4 to 100, on the inside of which a liquid film can flow down,
an upper distributor device for distributing liquid and gas into the individual tubes (1000),
a feed device (3100) for feeding a heating medium (20), preferably steam, pressurized water, oil or a salt melt, in particular steam, into the tube exterior space formed by the outside of the tubes (1000) and the shell (2000),
a discharge device (3200) for discharging cooled heating medium (21), in particular condensed water, from the tube exterior space,
a vapor offtake device (4100) for vapor (13) which is composed of the gas from the upper distributor device and vapor produced inside the tubes,
a liquid offtake device (4200) for residual liquid (14) which has not been vaporized inside the tubes,
a, preferably lower, device (5000) for separating and collecting residual liquid (14) and vapor (13),
wherein the upper distributor device for distributing liquid and gas into the individual tubes (1000) is the device (10 000) of the invention, the bottom (900) of the device (10 000) forms the upper tube plate of the falling film evaporator (100 000) and the n guide devices (800) are connected to the n tubes (1000) at the upper end thereof or the n guide devices (800) are constituents of the n tubes (1000).

Since the distributor device (10 000) of the invention is a constituent of the falling film evaporator (100 000) of the invention, the latter is of course, like the former, likewise upright and likewise preferably has a rotationally symmetric, particularly preferably round, in particular circular cross-sectional area. The "vapor (13)" is composed of the gas phase (11) which flows from the upper distributor device (10 000) through the guide devices (800) into the tubes (1000) and vapor produced inside the tubes. The gas phase (11) consists in the simplest case of the vapor formed by partial vaporization of the fluid (10). However, it can also, as indicated above in connection with the distributor device (10 000) of the invention, contain foreign gases or even consist of these. In the latter two cases the stream (13) strictly speaking does not consist only of vapor; however, since the main constituent of the stream 13 is vapor produced inside the tubes, the term "vapor" will be used for the stream 13 for reasons of simplifying the language.

Figure 5:
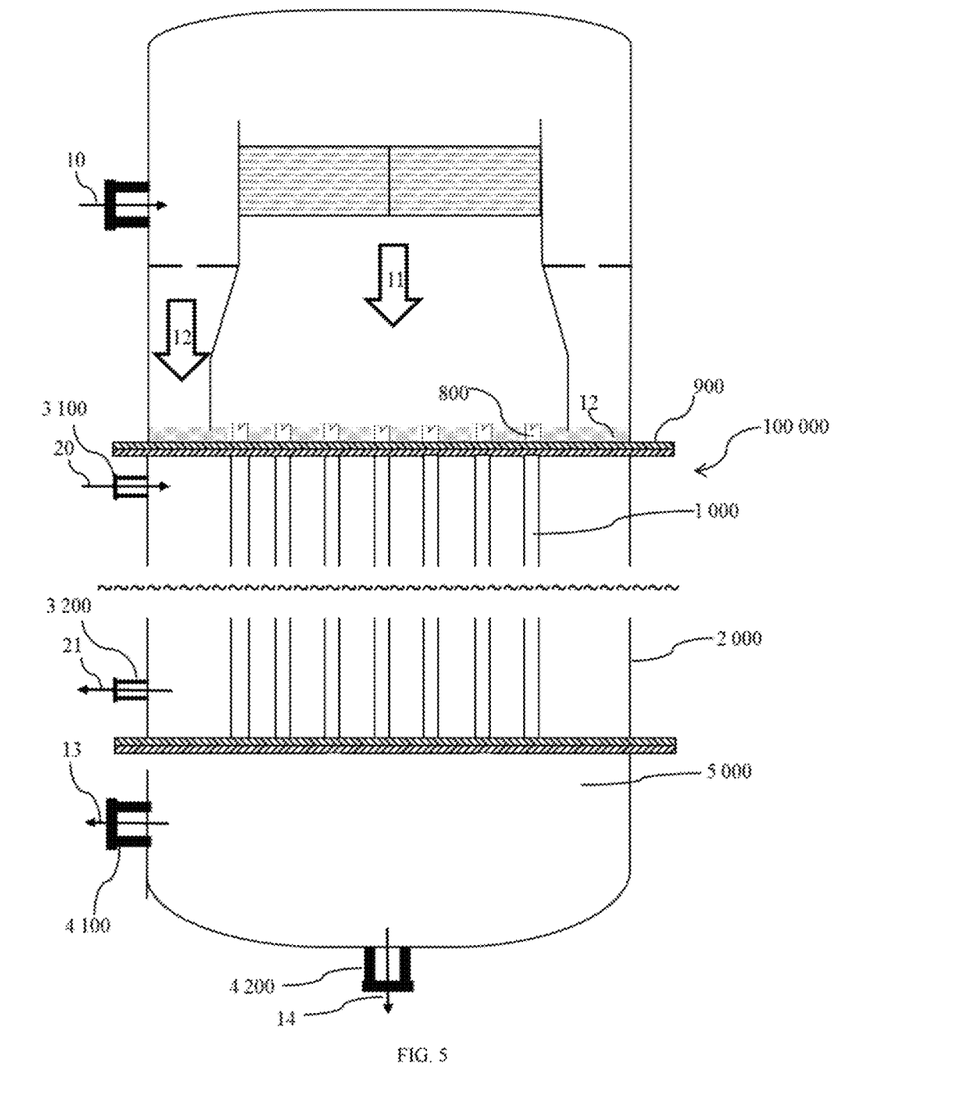
FIG. 5 illustrates an embodiment of a falling film evaporator of the invention.

With the exception of the upper distributor device (10 000), the falling film evaporator (100 000) of the invention corresponds to falling film evaporators of the prior art and can be constructed like these. The device (5000) for separating and collecting residual liquid (14) and vapor (13) can, as shown in FIG. 5, be fastened directly on the lower tube plate. However, it is also possible for the tubes (1000) to open into a joint tube section which goes over into the device (5000) which is then arranged, for example, next to the tube segment made up of n tubes (instead of underneath it).

Figure 6A:
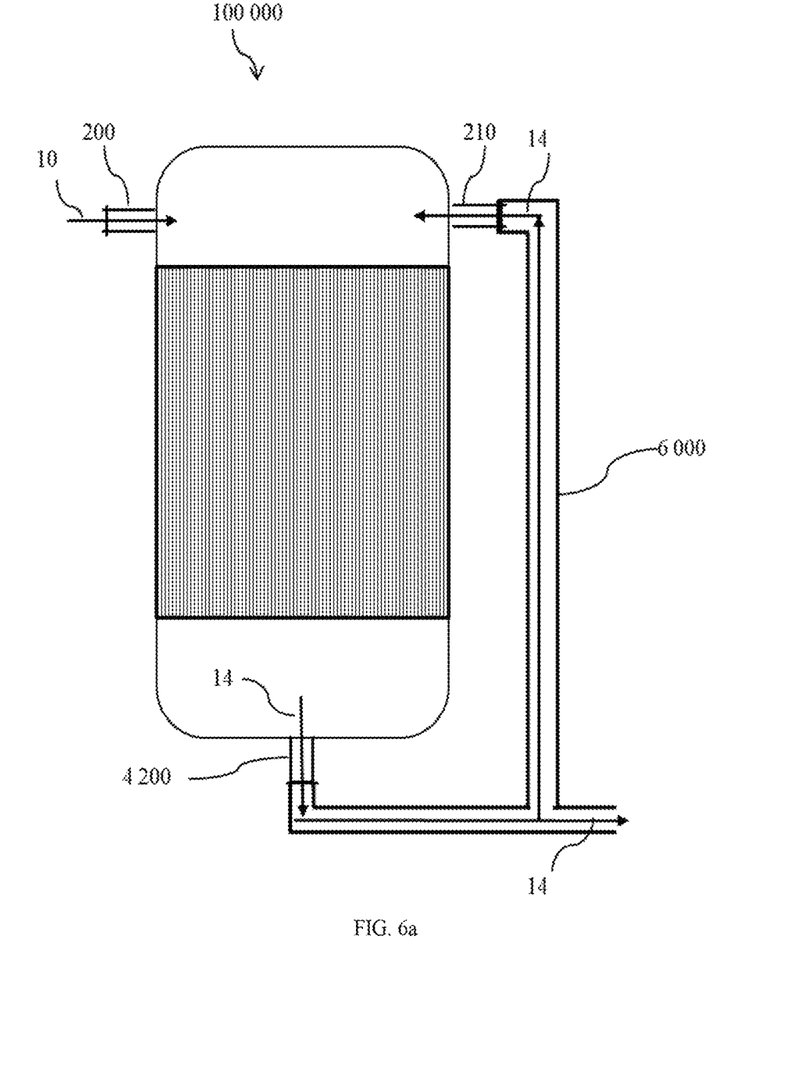
FIGS. 6a and 6b illustrate an embodiment of a falling film evaporator of the invention operated in circulation mode with a return device.
Figure 6B:
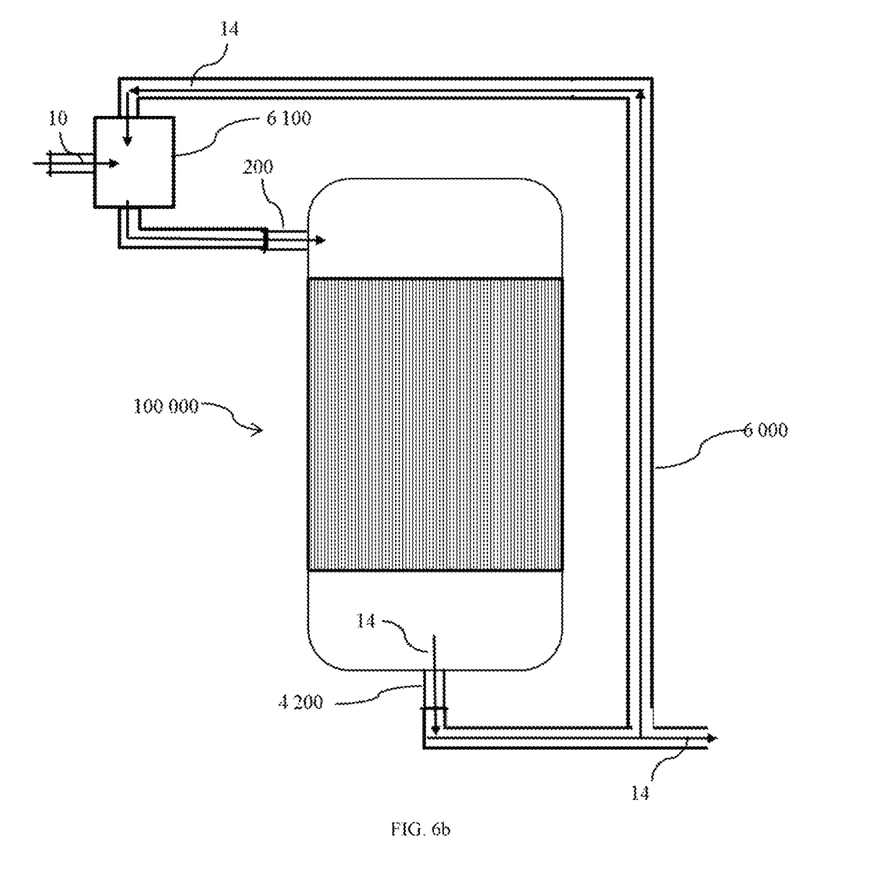

The falling film evaporator (100 000) of the invention can also be operated in the circulation mode with a return device (pump circulation conduit) (6000) (cf. FIG. 6a, b; in the interests of clarity, many details from FIG. 5 have been omitted; likewise, the peripheral equipment items such as pumps have not been drawn in). Part of the residual liquid (14) taken off at the bottom is then returned to the top of the falling film evaporator, either via a separate entry port (210) (FIG. 6a) or after mixing the residual liquid (14) with the feed stream (10) in a mixing device (6100); cf. FIG. 6b. The separate entry port (210) is preferably likewise installed so that tangential inflow is made possible and is, in particular, oriented in the same way as the entry port 200. In operation in the circulation mode, the temperature of the fluid (10) is preferably lower than the temperature of the circulated residual liquid (14). The comparatively cold fluid (10) is heated by contact with the comparatively hot residual liquid (14), so that spontaneous evaporation occurs.

The falling film evaporator of the invention can also be used as constituent of another apparatus, for example as vaporizer in a distillation column.

The mode of operation (in particular the conditions of pressure and temperature) of the falling film evaporator (100 000) of the invention depends on the type of material being evaporated. Here, a person skilled in the art will make recourse to the experience reported in the prior art in respect of the particular material to be evaporated and if necessary optimize this by means of simple routine tests. When the falling film evaporator (100 000) is operated under a pressure below ambient pressure, a suitable vacuum system which can easily be designed by a person skilled in the art for the particular application and is preferably connected to the vapor offtake device (4100) is used.

In principle, the distributor device (10 000) of the invention and in particular the falling film evaporator (100 000) according to the invention can be used in any systems, especially systems which have a tendency to form deposits, in which liquid fractions and gaseous fractions occur (e.g. as a result of spontaneous evaporation). Of course, use in systems without a particular tendency to form deposits is likewise possible. Systems having a high viscosity can likewise usefully be employed. This applies particularly to processes for the production and/or work-up of chemical products. Chemical products in the production and/or work-up of which the invention can be used are, in particular, organic nitro compounds, primary organic amines, isocyanates, polyether polyols and polycarbonates. Fields of use for the falling film evaporator of the invention, either alone or optionally in combination with other apparatuses such as distillation columns, can be, for example, distillation (e.g. of organic nitro compounds or of isocyanates), drying (e.g. of organic primary amines or polyether polyols) or devolatilization (e.g. of solvent-containing polycarbonate melts).

Particular preference is given to use in the production and/or work-up of isocyanates and precursors thereof, namely the corresponding organic primary amines and organic nitro compounds. Examples of suitable isocyanates are tolylene diisocyanate (TDI; in particular meta-TDI), the diisocyanates and polyisocyanates of the diphenylmethane series (MDI), hexamethylene diisocyanate (HDI), pentamethylene diisocyanate (PDI), isophorone diisocyanate (IPDI), xylylene diisocyanate (XDI, in particular meta-XDI), naphthalene diisocyanate (NDI or, for example, "Desmodur 15" from Covestro Deutschland AG), and dicyclohexylmethane diisocyanate (HMDI). The work-up, for example, of crude isocyanates thus normally comprises steps in which it is necessary to vaporize the isocyanate to be purified. Apart from a simple distillation to separate off impurities, the vaporization of the isocyanate to at least partially remove the latter from a residue-containing distillation bottoms stream from isocyanate production and/or for separating a monomeric isocyanate fraction, which is vaporized, from a polymeric isocyanate fraction are worthy of particular mention as useful fields of application for the invention.

Regardless of the precise configuration of the distillative work-up of crude isocyanates, at least one distillation bottoms stream is also obtained in addition to the pure isocyanate isolated (in general as distillate stream). This distillation bottoms stream contains the so-called distillation residue and proportions of the isocyanate to be produced. The distillation residue contains compounds which do not vaporize under the conditions of pressure and temperature selected for the distillation or cannot be vaporized at all without decomposition. The compounds which are difficult or even impossible to vaporize and are present in the distillation residue are, unless they are impurities from the primary amine used which have passed unchanged through the phosgenation process, relatively high molecular weight phosgenation products, the structure of which is not always known precisely. The compounds here can thus be compounds which can (formally) be derived from polymerization products of the amine used by replacement of the unpolymerized amine groups by isocyanate groups. The distillation bottoms stream containing the distillation residue is usually worked up, with this work-up usually also comprising a step of partial vaporization of the isocyanate which is to be produced and is present in the distillation bottom stream, leaving a liquid stream which is depleted in the isocyanate to be produced and is usually dried further. The vaporization step mentioned can be carried out very well in the falling film evaporator of the invention. This vaporization is preferably carried out at a temperature in the range from 120° C. to 180° C. and a pressure in the device (5000) for separating and collecting residual liquid (14) and vapor (13) in the range from 20 mbar$_{(abs.)}$ to 60 mbar$_{(abs.)}$, particularly preferably at a temperature in the range from 130° C. to 175° C. and a pressure in the range from 25 mbar$_{(abs.)}$ to 45 mbar$_{(abs.)}$. The above-described use of the falling film evaporator of the invention is particularly suitable for isolating TDI from TDI-containing distillation bottoms streams.

As an example of the separation of a monomeric isocyanate fraction, which is vaporized, from a polymeric isocyanate fraction as field of use for the present invention, mention may be made of the separation of monomeric IPDI from corresponding trimers (e.g. "Desmodur Z" from Covestro Deutschland AG).

EXAMPLES

Experiments were carried out for a liquid distributor on an industrial scale using a water/air mixture as test system. The test apparatus used, by means of which the conditions in a falling film evaporator were simulated, had a diameter of about 900 mm and 45 tubes. In order to examine the influence of spontaneous evaporation on the liquid distribution, 6 m³/h of pure water (situation without spontaneous evaporation) were introduced in one case and 6 m³/h of water plus 560 or 1000 m³/h of air were introduced via the tangential entry port (situation with spontaneous evaporation) in the other case. In all cases, the liquid volume flows per tube were measured and the standard deviation was determined according to the following equation:

$$\text{Standard deviation: } Cv = \left[ \frac{\sum \left( \frac{x_i - \bar{x}}{\bar{x}} \right)^2}{n - 1} \right]^{1/2} \times 100 [\%]$$

The symbols here have the following meanings: $x_i$ is the measured liquid volume flow per tube, $\bar{x}$ is the arithmetic mean of the measured liquid volume flows over all n tubes and n is the number of tubes The distributor was, in all experiments, operated with a liquid level of 50 mm on the tube plate and using tube spouts having tangential inflow slits (rectangular slits having a slit width of 5 mm).

Example 1 (Liquid Distribution with and without Spontaneous Evaporation without Swirl Breaker (600); Comparison)

Figure 7:
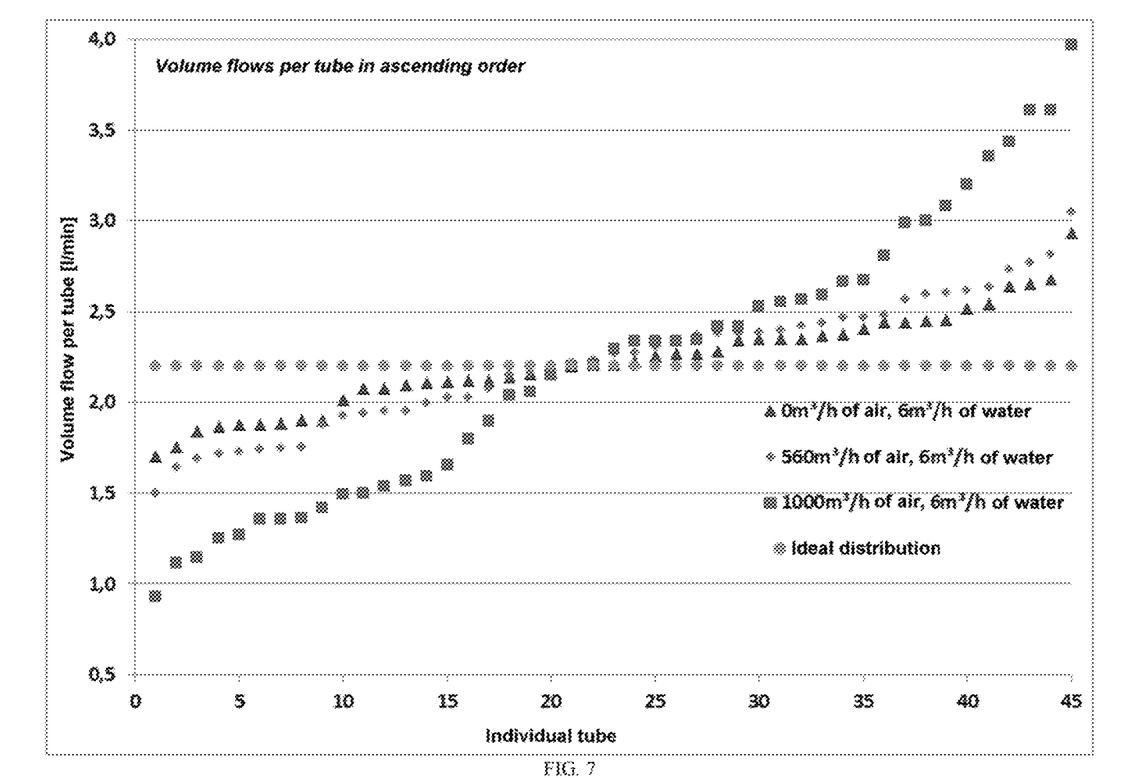
FIG. 7 is a graph illustrating measured volume flow per tube for comparison Example 1.

A swirl breaker (600) was not used. In the outer annular gap (400) a swirl breaker (700) having a continuous slit for the liquid was used (as depicted in FIG. 2b). The measured volume flow per tube in ascending order are shown in FIG. 7. It can clearly be seen that the distribution deviates ever further from the optimum distribution with increasing proportion of gas phase (corresponding to increasing spontaneous evaporation). At 1000 m³/h, the relative standard deviation is 34%, which is very high for distributors on an industrial scale. At 0 m³/h of air, the standard deviation is 12% and is in the region of normal standard deviations for industrial liquid distributors.

The experiments show that the gas phase greatly disrupts the distribution of the liquid over the tubes, even though gas and liquid were separated cleanly directly after entry into the cap and the liquid is predistributed by the swirl breaker (700).

Example 2 (Liquid Distribution with Spontaneous Evaporation Using Swirl Breaker (600) for the Gas Phase (11); According to the Invention)

Figure 8:
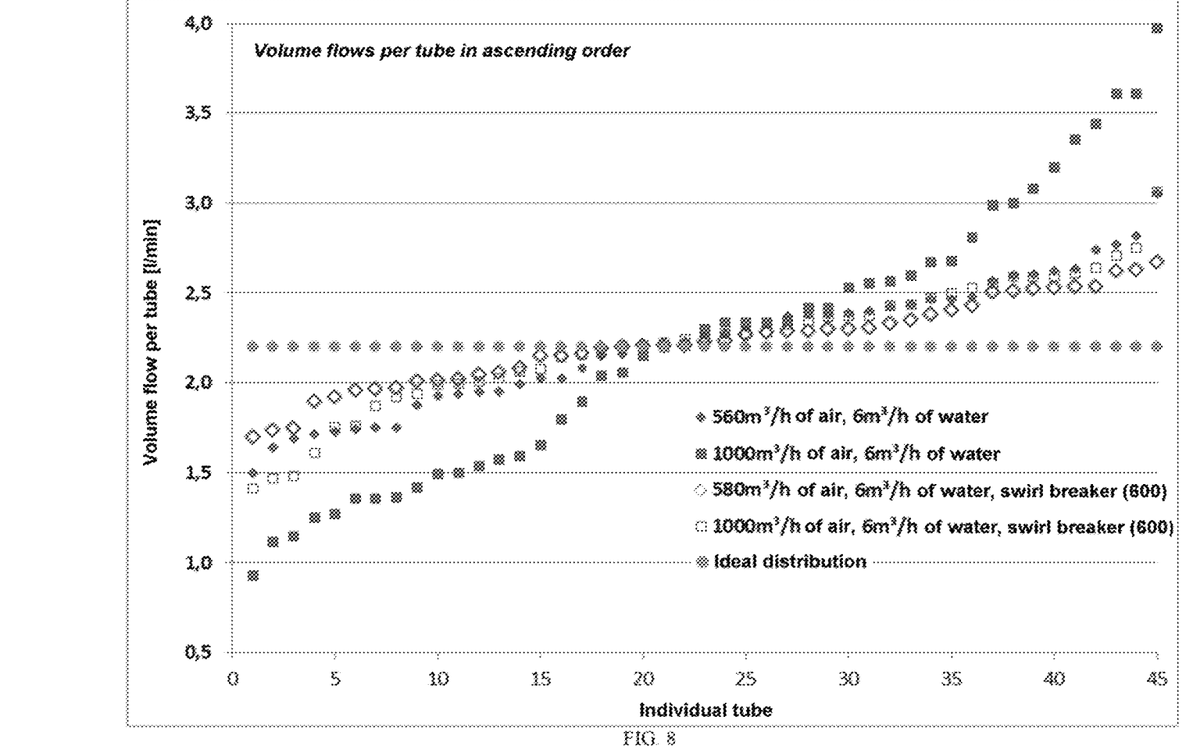
FIG. 8 is a graph illustrating measured volume flow per tube for comparison Example 1 and Example 2.

The experiments using 560 m³/h and 1000 m³/h of air of example 1 were repeated after installation of the swirl breaker (600). A significant improvement in the liquid distribution is found here—see FIG. 8 (the results from example 1 are also shown for better comparison). At 1000 m³/h, the relative standard deviation can in this way be reduced from the previous 34% to 16%. The distribution achieved here is close to the distribution using 0 m³/h of air in example 1. The example thus shows that the negative influence of the air on the liquid distribution can be virtually eliminated by the use of the swirl breaker (600). In the example, a simple swirl breaker (600) having 4 blades was used; this can be optimized further (e.g. 8 blades in order to calm the air flow (in general: the gas flow) to a greater extent).

In example 2 according to the invention, the liquid distribution could thus be improved significantly compared to example 1 without the liquid being calmed completely on the tube plate (900). Instead, significant circulatory flow in the liquid, which avoids the formation of deposits in systems having a tendency to form them, continues to be visible.

The invention claimed is:

1. A device suitable for uniform division of a fluid into n fluid streams each containing gas and liquid, where n is a natural number greater than or equal to 2, the device comprising:
    (a) an upright cap bounded at the bottom by a plate;
    (b) an entry port arranged in a lateral delimiting wall of the upright cap, the entry port configured to bring about tangential inflow of the fluid entering therein;
    (c) an internal arranged upright in the interior of the cap, wherein the internal:
        (i) together with the interior wall of the cap, forms an annular gap for downflowing liquid,
        (ii) comprises an upper edge that ends above the entry port and below an upper delimitation of the upright cap so that the upper edge of the internal and the upper delimitation of the cap form a passage for downward-flowing gas,
        (iii) has, at the top thereof, at least one upper opening for the downward-flowing gas flowing therein,
        (iv) comprises a lower edge that ends above the plate so that the lower edge of the internal and the plate form a passage for the downflowing liquid, and
        (v) comprises at least one opening at the bottom thereof that is hydrodynamically connected to the at least one upper opening; and
    (d) n guide devices, wherein the guide devices protrude through the at least one opening at the bottom of the internal into the internal and the guide devices comprise liquid entry openings and gas entry openings;
    wherein a swirl breaker for the downward-flowing gas stream is arranged in the interior of the internal, the swirl breaker being configured to reduce or eliminate turbulence in the downward-flowing gas stream and to reduce the rotational energy of downward-flowing gas stream.

2. The device of claim 1, wherein the internal has a cross section that widens in a downward direction.

3. The device of claim 1, wherein a swirl breaker for liquid having through-openings is arranged in the annular gap below the entry port, the through-openings being configured to allow flow of the downflowing liquid therethrough.

4. The device of claim 3, wherein the swirl breaker for liquid is a metal plate in which the through-openings are formed by at least two holes distributed uniformly over the entire area of the plate and/or by at least one slit that runs through the entire area of the plate.

5. The device of claim 1, wherein the at least one upper opening extends over the entire internal cross section of the internal and/or the at least one opening through which the n guide devices protrude into the internal extends over the entire internal cross section of the internal.

6. The device of claim 1, wherein then guide devices are tube spouts or constituents of tubes.

7. The device of claim 6, wherein the liquid entry openings:
    (i) are tangential slits arranged so that the flow of the downflowing liquid produced on the inside of the guide devices has the same direction as the flow of the downflowing liquid produced in the annular gap by the arrangement of the entry port, or
    (ii) are axial slits.

8. The device of claim 1, wherein the swirl breaker for the downward-flowing gas stream is selected from the group consisting of a swirl cross, a packing, a knitted wire mesh, a perforated plate, and a deflection plate.

9. The device of claim 1, wherein the n guide devices protrude to a height in the range from 10 mm to 100 mm into the internal.

10. A falling film evaporator comprising:
    (a) an outer, enclosing shell,
    (b) n tubes fastened in an upper tube plate and a lower tube plate, where n is a natural number greater than or equal to 2, configured so that on the inside of which a liquid film can flow down,
    (c) an upper distributor device configured to distribute liquid and gas into the individual tubes,
    (d) a feed device configured to feed a heating medium into a tube exterior space formed by the outside of the tubes and the shell,
    (e) a discharge device configured to discharge cooled heating medium from the tube exterior space,
    (f) a vapor offtake device configured to offtake vapor,
    (g) a liquid offtake device configured to offtake residual liquid not vaporized inside the tubes, and
    (h) a device configured to separate and collect the residual liquid and the vapor, wherein the upper distributor device is the device of claim 1, where the bottom of the device forms the upper tube plate of the falling film evaporator and then guide devices are joined to the n tubes at the upper end thereof or the n guide devices are constituents of the n tubes.

11. The falling film evaporator of claim 10, further comprising a return device configured to recirculate part of the residual liquid into the distributor device, where the return device:
    (i) comprises a mixing device configured to mix the recirculated part of the residual liquid with the fluid before entry into the distributor device, or (ii) opens into an entry port that is different from the entry port and is arranged in a lateral delimiting wall of the cap.

12. A process for producing and/or working-up of a chemical product selected from the group consisting of organic nitro compounds, organic primary amines, isocyanates, polyether polyols and polycarbonates, comprising using the device of claim 1.

13. A process for producing and/or working-up of a chemical product selected from the group consisting of organic nitro compounds, organic primary amines, isocyanates, polyether polyols and polycarbonates, comprising using the falling film evaporator of claim 10.

14. The process of claim 13, comprising using the falling film evaporator in the work-up of an isocyanate for vaporization of the isocyanate.

15. The process of claim 14, comprising using the vaporization of the isocyanate to (i) at least partially remove the isocyanate from a residue-containing distillation bottoms stream from isocyanate production, and/or (ii) to separating a monomeric isocyanate fraction, which is vaporized, from a polymeric isocyanate fraction.

16. The process of claim 14, wherein the isocyanate is selected from the group consisting of tolylene diisocyanate, a diisocyanate and/or polyisocyanate of the diphenylmethane series, hexamethylene diisocyanate, pentamethylene diisocyanate, isophorone diisocyanate, xylylene diisocyanate, naphthalene diisocyanate, and dicyclohexylmethane diisocyanate.

17. The process of claim 15, wherein the isocyanate is selected from the group consisting of tolylene diisocyanate, a diisocyanate and/or polyisocyanate of the diphenylmethane series, hexamethylene diisocyanate, pentamethylene diisocyanate, isophorone diisocyanate, xylylene diisocyanate, naphthalene diisocyanate, and dicyclohexylmethane diisocyanate.

* * * * *